United States Patent [19]

Engel

[11] 4,024,277

[45] May 17, 1977

[54] PHOSPHORO-AMINOSULFENYL DERIVATIVES OF BENZOFURAN CARBAMATES

[75] Inventor: John Francis Engel, Medina, N.Y.

[73] Assignee: FMC Corporation, Philadelphia, Pa.

[22] Filed: Oct. 16, 1975

[21] Appl. No.: 623,195

[52] U.S. Cl. .......................... 424/285; 260/346.2 R
[51] Int. Cl.$^2$ ................. C07D 307/86; A01N 9/28
[58] Field of Search .............. 260/346.2 R; 424/285

[56] References Cited

OTHER PUBLICATIONS

Fahmy et al., J. Agr. Food Chem., vol. 18, No. 5, (1970), pp. 793–796.
Hackh's Chemical Dictionary, (1969), pp. 60 and 62.
Gould, Mechanism and Structure in Organic Chem., Holt, Rhinehart and Winston, New York, (1959), pp. 412–418.

*Primary Examiner*—Henry R. Jiles
*Assistant Examiner*—Bernard Dentz
*Attorney, Agent, or Firm*—Flynn & Frishauf

[57] ABSTRACT

A new class of compounds comprising [(N-disubstituted phosphoro)-(N-alkyl)aminosulfenyl]-substituted carbamic acid esters of 2,3-dihydro-7-benzofuranol exhibit outstanding insecticidal activity. The preparation of these compounds, their physical properties, formulation and use to control both household insects and crop pests are exemplified.

14 Claims, No Drawings

PHOSPHORO-AMINOSULFENYL DERIVATIVES OF BENZOFURAN CARBAMATES

FIELD OF INVENTION

This invention has to do with the general field of pesticides and in particular to insecticides for the control of insects which attack crops and animals and of insects which are disease vectors.

BACKGROUND OF THE INVENTION

Carbamic acid esters of various types are well known and several types have been found to be useful as pesticides, including as insecticides. Carbofuran — the common name for 2,3-dihydro-2,2-dimethyl-7-benzofuranyl methyl-carbamate — is described in U.S. Pat. No. 3,474,171, and is shown therein to be effective in control of beetles, true bugs, aphids and acarids. Products from reaction of amines with N-chlorothio carbamates containing a 2,3-dihydro7-benzofuranyl group, are also indicated to be useful as pesticides in U.S. Pat. No. 3,843,689. Phosphorus derivatives of carbofuran in which the phosphorus moiety is directly linked to the carbamate nitrogen, have also been reported to have insecticidal activity (J. Agr. Food Chem., Vol. 18, No. 5, 1970, pp. 793–796).

SUMMARY OF THE INVENTION

In accordance with the present invention, there are provided compounds of the formula

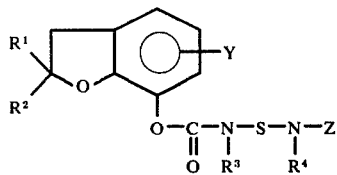

wherein
$R^1$ and $R^2$ are each hydrogen or lower alkyl ($C_1$ to $C_6$) and can be the same or different;
$R^3$ is lower alkyl ($C_1$ to $C_6$ alkyl);
$R^4$ is hydrogen, lower alkyl ($C_1$ to $C_6$), cycloalkyl ($C_3$–$C_8$), aralkyl or aryl; and

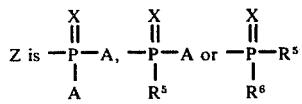

where
X is O or S, A is $OR^5$, $SR^5$, $NHR^5$ or $NR^5R^6$, and $R^5$ and $R^6$ are each alkyl, cycloalkyl or aryl and can be the same or different;
Y is hydrogen, halo or methyl.

These compounds are [(N-disubstituted phosphoro)(N-alkyl)aminosulfenyl]-substituted carbamic acid esters of 2,3-dihydro-7-benzofuranol.

PARTICULAR EMBODIMENTS OF THE INVENTION

Compounds of this invention, and identified below by (IV), can be prepared by syntheses such as illustrated below.

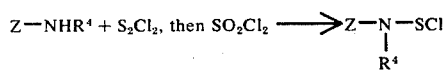

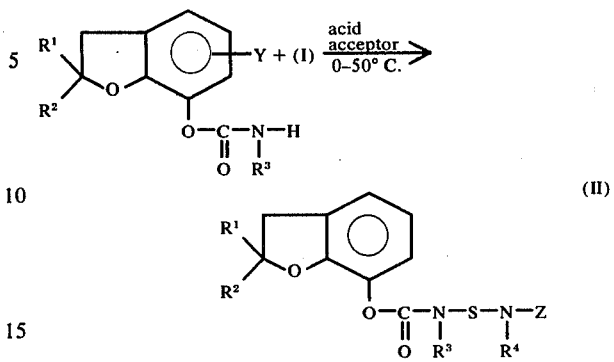

Compounds represented by $Z-NHR^4$ can be prepared by procedures given in Houben-Weyl, Book XII/2.

In the preparation of compounds (II), a 2,3-dihydro-7-benzofuranol having the aforementioned $R^1$ groups is employed. Particularly preferred is the 2,2-dimethyl compound.

In the preparation of compounds represented by (II), temperatures range from about 0° C. to about 50° C., preferably 20°–30° C. An acid acceptor is included in the reaction mixture, the acceptor being an organic base such as pyridine or a trialkylamine such as triethylamine, or an inorganic base such as sodium or potassium carbonate. The quantity of acceptor is substantially equimolar related to compound (II).

The 2,3-dihydro-7-benzofuranol and compound (II) are preferably used in substantially equimolar amounts; however, a slight excess of (II) is advantageous to assure complete conversion of the carbamate. However, such reactants can be employed in ratios of from about 1.0 : 1 to about 1.2 : 1, respectively.

An inert diluent can be included in the reaction to form compound (II). Suitable diluents include benzene, toluene, diethyl ether, dioxane, chloroform, methylene chloride, dimethylacetamide, 1,2-dimethoxyethane, and ethyl acetate. In general, essentially any solvent devoid of active hydrogen is suitable.

The preparation and insecticidal properties of the compounds of this invention are illustrated in the following specific examples, which are provided only by way of illustration and not of limitation. Unless otherwise specified, all temperatures are in degrees centigrade, all parts are by weight, and concentration of liquid volume was carried out under the reduced pressure produced by a water aspirator.

EXAMPLE 1 a. Synthesis of 0,0-diethyl N-methylphosphoramidate intermediate

To a solution of 86.2 grams of diethyl chlorophosphate in 500 ml. of diethyl ether, was added 34.1 g. of methylamine during 1 hour. The reaction temperature was maintained below 10° C. during the addition. Upon complete addition, the reaction mixture was allowed to warm to ambient temperature, about 20° C., during 1 hour, where it was stirred for an additional 1 hour. The resulting reaction mixture was filtered and the filtrate therefrom was evaporated to dryness under reduced pressure. The residual oil so obtained was distilled, under reduced pressure, to give 59.91 g. of 0,0-1 diethyl

N-methylphosphoramidate; b.p. = 85°–90° C./0.19–0.27 mm. Hg.

The ir spectrum was consistent with the assigned structure.

b. Synthesis of (N-diethoxyphosphinyl) (N-methyl)-amidosulfenyl chloride intermediate To a solution of 21.7 g. of the 0,0-diethyl N-methylphosphoramidate obtained in (a) and 18.2 ml. of triethylamine in 300 ml. of dry benzene was added 5.25 ml. of sulfur monochloride. The reaction temperature was maintained between 0°–5° C. Upon complete addition, the reaction mixture was stirred at this temperature during 1 hour, then filtered. The filtrate was evaporated to dryness under reduced pressure at a temperature below 40° C. The red viscous oil so obtained was cooled in an ice-water bath, and 5.3 ml. of sulfuryl chloride was added. The resulting reaction mixture was warmed at 35°–38° C., during 15 minutes. By-product sulfur dioxide was removed under aspirator vacuum. The residue was distilled under vacuum, to give 17.46 g. of [N-diethoxyphosphinyl) (N-methyl)]-amidosulfenyl chloride; b.p. = 72°–82° C./0.11 mm. Hg.

c. Synthesis of 2,3-dihydro-2,2-dimethyl-7-benzofuranyl [(N-diethoxyphosphinyl) (N-methyl)-aminosulfenyl][methyl]carbamate To 11.7 g. of (N-diethoxyphosphinyl) (N-methyl)-amidosulfenyl chloride obtained in (b) above, cooled to 0° C., was added dropwise with stirring 8.8 g. of carbofuran in 100 ml. of pyridine. Upon complete addition, the reaction mixture was allowed to warm to ambient temperature (about 20° C.) during 18 hours. The resulting reaction mixture was filtered, and approximately one-half of the filtrate was added to 50 ml. of water. The mixture was extracted with three portions of 50 ml. each of chloroform. The combined extracts were washed with three portions of 25 ml. each of 10% hydrochloric acid, then two portions of 25 ml. each of saturated aqueous sodium bicarbonate, and finally one portion of 25 ml. of water. The resulting organic layer was dried using sodium sulfate, and filtered. The filtrate was evaporated to dryness under reduced pressure. The second one-half of the filtrate was processed in an identical manner and combined with the like crude product to give a total of 13.9 g. of crude product. The crude product was purified in seven fractions from a chromatographic column of 70 g. of silica gel eluted with 10% toluene — 90% hexane to 100% toluene; then 20% chloroform — 80% toluene to 100% chloroform. The yield was 5.23 grams of purified 2,3-dihydro-2,2-dimethyl-7-benzofuranyl [(N-diethoxyphosphinyl)(N-methyl)aminosulfenyl][methyl]carbamate.

The nmr and the ir spectra were consistent with the assigned structure.

Analysis calculated for $C_{17}H_{27}N_2O_6PS$ is: C 48.79; H 6.50; and N 6.69;

found: C 48.74; H 6.61; and N 6.66.

EXAMPLE 2 a. Synthesis of di-n-propyl phosphorochloridate intermediate

To 100 ml. of dry benzene, at ambient temperature (about 20° C.), was added 60 grams of propanol. This mixture was cooled to 5°–10° C., and to it was added 48.1 g. of phosphorus trichloride in 100 ml. of dry benzene. The reaction mixture was stirred during 1 hour while maintaining the 5°–10° C. reaction mixture temperature. To this was added 47.3 g. of sulfuryl chloride in 100 ml. of dry benzene. Upon complete addition the reaction mixture was allowed to warm to ambient temperature, where it was stirred during 1 hour. Evaporation of the reaction mixture to dryness under reduced pressure gave crude product. Vacuum distillation of the crude product gave 57.18 g. of di-n-propyl phosphorochloridate; b.p. = 63°–68° C./0.35 mm.

The ir spectrum was consistent with the assigned structure.

b. Synthesis of 0,0-di-n-propyl N-methylphosphoramidate intermediate

This compound was prepared in the manner of Example 1(a). Distillation gave 22.87 g. of pure 0,0-di-n-propyl N-methyl-phosphoramidate; b.p. 98° C./0.25 mm. Hg.

c. Synthesis of (N-di-n-propoxyphosphinyl)(N-methyl)amidosulfenyl chloride intermediate This compound was prepared in the manner of Example 1(b).

d. Synthesis of 2,3-dihydro-2,2-dimethyl-7-benzofuranyl [(N-di-n-propoxyphosphinyl) (N-methyl)aminosulfenyl][methyl]carbamate This compound was prepared in the manner of Example 1(c). Pure 2,3-dihydro-2,2-dimethyl-7-benzofuranyl [(N-di-n-propoxyphosphinyl) (N-methyl)aminosulfenyl][methyl]carbamate was obtained in nine fractions from a silica gel chromatographic column eluted with 20% toluene — 80% hexane to 100% toluene, then 25% chloroform — 75% toluene to 100% chloroform.

The nmr and the ir spectra were consistent with the assigned structure.

Analysis calculated for $C_{19}H_{31}N_2O_6PS$ is: C 51.10; H 7.00; and N 6.28;

Found: C 51.12; H 6.77; and N 5.92.

EXAMPLE 3 a. Synthesis of 0,0-di-n-propyl N-n-propylphosphoramidate intermediate

This compound was prepared in the manner of Example 1(a) to give 23.75 grams of 0,0-di-n-propyl N-n-propylphosphoramide; b.p. = 111° C./0.26 mm.

The ir spectrum was consistent with the assigned structure.

b. Synthesis of (N-di-n-propoxyphosphinyl)(N-n-propyl)amidosulfenyl chloride intermediate This compound was prepared in the manner of Example 1(b) but, because it its instability at elevated temperature, was used without final purification.

c. Synthesis of 2,3-dihydro-2,2-dimethyl-7-benzofuranyl [N-di-n-propoxyphosphinyl)(N-n-propyl)aminosulfenyl][methyl]carbamate This compound was prepared in the manner of Example 1(c). Pure 2,3-dihydro-2,2-dimethyl-7-benzofuranyl [(N-di-n-propoxyphosphinyl) (N-n-propyl)aminosulfenyl][methyl]carbamate was obtained in 12 fractions from a chromatographic column of 140 grams of silica gel eluted first with 20% toluene — 80% hexane to 100% toluene, then 25% chloroform — 75% toluene to 100% chloroform.

The nmr spectrum was consistent with the assigned structure.

Analysis calculated for $C_{21}H_{35}N_2O_6PS$ is: C 53.15; H 7.43; and N 5.90;

found: C 52.74; H 7.50; and N 5.84.

EXAMPLE 4 a. Synthesis of 0,0-diethyl N-n-propylphosphoramidate intermediate

This compound was prepared in the manner of Example 1(a). It has a boiling point of 111° C./0.26 mm; its ir spectrum is consistent with the assigned structure.

b. Synthesis of (N-diethoxyphosphinyl) (N-n-propyl)amidosulfenyl chloride intermediate This compound was prepared in the manner of Example 1(b) but, because of its instability at elevated temperature, was used without final purification.

c. Synthesis of 2,3-dihydro-2,2-dimethyl-7-benzofuranyl [(N-diethoxyphosphinyl) (N-n-propyl)aminosulfenyl][methyl]carbamate This compound was prepared in the manner of Example 1(c). Pure 2,3-dihydro-2,2-dimethyl-7-benzofuranyl [(N-diethoxyphosphinyl) (N-n-propyl)aminosulfenyl][methyl]carbamate was obtained in six fractions from a chromatographic column of silica gel eluted with first 20% toluene — 80% hexane, then 75% chloroform — 25% toluene to 100% chloroform.

The nmr and the ir spectra were consistent with the assigned structure.

Analysis calculated for $C_{19}H_{31}N_2O_6PS$ is: C 51.11; H 7.00; and N 6.27;

found: C 50.93; H 6.74; and N 6.23.

EXAMPLE 5 a. Synthesis of 0,0-dimethyl N-ethylphosphoramidate intermediate

This compound was prepared according to the procedure given in Example 1(a), above. The liquid so obtained has a boiling point of 80°-85° C./0.31 mm. The ir spectrum was consistent with the assigned structure.

b. Synthesis of (N-dimethoxyphosphinyl) (N-ethyl)amidosulfenyl chloride intermediate This intermediate was prepared from the liquid of (a) according to the procedure given in Example 1(b), above; however, because of its instability at elevated temperature, it was used without final purification.

c. Synthesis of 2,3-dihydro-2,2-dimethyl-7-benzofuranyl [(N-dimethoxyphosphinyl) (N-ethyl) aminosulfenyl][methyl]carbamate This compound was prepared from the intermediate obtained in (b) in accordance with the procedure described in Example 1(c), above. The pure compound was obtained in four fractions from a chromatographic column of silica gel using chloroform as solvent throughout.

The ir and nmr spectra were consistent with the assigned structure.

Analysis calculated for $C_{16}H_{25}N_2O_6PS$ is: C 47.52; H 6.23; and N 6.93;

found: C 48.05; H 6.06; and N 6.58.

EXAMPLES 6 through 9 are presented in summary form, the compounds identified being formed in the same manner as described in the preceding EXAMPLES.

EXAMPLE 6 a. 0,0-Diisopropyl N-methylphosphoramidate, b.p. 80°-84°/0.30 mm.

b. (N-Diisopropoxyphosphinyl) (N-methyl)amidosulfenyl chloride — not purified c. 2,3-Dihydro-2,2-dimethyl-7-benzofuranyl [(N-diisopropoxyphosphinyl) (N-methyl)aminosulfenyl][methyl]carbamate — purified by silica gel column chromatography using chloroform as solvent; ir and nmr spectra were consistent with assigned structure.

Analysis calculated for $C_{19}H_{31}N_2O_6PS$ is:

C 51.11; H 7.00; and N 6.27;

found: C 51.31; H 6.76; and N 6.15.

EXAMPLE 7 a. 0,0-Diphenyl N-propylphosphoramidate, m.p. 55°-57°; ir and nmr spectra were consistent with the assigned structure.

Analysis calculated for $C_{15}H_{18}NO_3P$ is:

C 61.85; H 6.23; and N 4.81;

found: C 62.10; H 6.24; and N 4.67.

b. (N-Diphenoxyphosphinyl) (N-propyl)amidosulfenyl chloride — not purified c. 2,3-Dihydro-2,2-dimethyl-7-benzofuranyl [(N-diphenoxyphosphinyl) (N-methyl)aminosulfenyl][methyl]carbamate — purified by silica gel column chromatography using a 40% chloroform-60% toluene mixture as eluting solvent in initial purification, and toluene in the second purification; the product from column chromatography was recrystallized from hexane containing a small amount of toluene; the purified product has a melting point of 114°-116°; ir and nmr spectra were consistent with the assigned structure.

Analysis calculated for $C_{27}H_{31}N_2O_6PS$ is: C 59.76; H 5.76; and N 5.16;

found: C 59.47; H 5.77; and N 5.41.

EXAMPLE 8 a. 0,0-Diethyl N-ethylphosphoramidate, b.p. 97°-100°/0.35 mm.

b. (N-Diethoxyphosphinyl) (N-ethyl)amidosulfenyl chloride, b.p. 78°-80°/0.14 mm.

c. 2,3-Dihydro-2,2-dimethyl-7-benzofuranyl [(N-diethoxyphosphinyl) (N-ethyl)aminosulfenyl][methyl]carbamate — purified by silica gel column chromatography using toluene as initial eluent and followed by mixtures of increasing chloroform content to chloroform as final eluent; ir and nmr spectra were consistent with the assigned structure.

Analysis calculated for $C_{18}H_{29}N_2O_6PS$ is: C 49.99; H 6.76; and N 6.48;

found: C 50.10; H 6.81; and N 6.33.

EXAMPLE 9 a. 0,0-Diethyl N-(2-phenylethyl)phosphoramidate, b.p. 140°-143°/0.14 mm.

b. (N-Diethoxyphosphinyl) (N-2-phenylethyl)amidosulfenyl chloride — not purified c. 2,3-Dihydro-2,2-dimethyl-7-benzofuranyl [(N-diethoxyphosphinyl)(N-2-phenylethyl)aminosulfenyl]-[methyl-carbamate]— purified by silica gel column chromatography using hexane-toluene as the initial eluting solvent, following by toluene alone and progressing through toluene-chloroform mixtures to chloroform alone; product is a heavy oil; ir and nmr spectra were consistent with the assigned structure.

Analysis calculated for $C_{24}H_{33}N_2O_6PS$ is: C 56.68; H 6.54; and N 5.19;

found: C 56.39; H 6.78; and N 5.18.

EXAMPLE 10 a. Initial Insecticidal Activity

In this test, a candidate insecticide, in solution, is applied to either infested or uninfested plants or containers by spraying or dipping. (The preferred test procedure varies with insect species. The dipping method is better than the spraying method, and vice versa, for certain species of insects. Also some species are better adapted to the test by infesting after the chemical treatment rather than before.) Once the tests have been established, a 48-hour exposure period is observed before reading the tests. Insect species included in these tests are Mexican bean beetle (*Epilachna varivestis* Mulsant), pea aphid [*Acyrthosiphon pisum* (Harris)], southern armyworm [*Spodoptera eridania* (Cramer)], twospotted spider mite (*Tetranychus urticae* Koch), large milkweed bug [*Oncopeltus fasciatus* (Dallas)], plum curculio [*Conotrachelus nenuphar* (Herbst)], confused flour beetle (*Tribolium confusum* Jacquelin duVal) and granary weevil [*Sitophilus granarius* (Linnaeus)]. Test results are set forth in Table I. A control sample, comprising the solution without the candidate insecticide, is also included.

b. Seven-Day Residual Insecticidal Activity

In this test, a candidate insecticide, in solution, is applied to uninfested plants or containers by dipping or spraying. A seven-day holding period is necessary before infestation. A 48-hour exposure period is observed before evaluation of the tests. The insect species used in this type of test are the same as those listed under initial activity. Test results are given in Table II.

c. Systemic Insecticidal Acitivity (Soil/Water)

In this test, a candidate insecticide, in solution, is added to the soil of either uninfested pinto bean seedlings (*Phaseolus vulgaris*) or uninfested broad bean seedlings (*Vicia faba* var. Windsor). The plant species used depend on the insect species in the test. Usually, a 72-hour translocation period before infestation is required, followed by a 48-hour exposure period, before evaluation of the tests. The insect species used in the systemic tests are Mexican bean beetle, southern armyworm, pea aphid, and twospotted spider mite. Systemic insecticidal activity test results are shown in Table III.

d. Ovicidal Activity Against the Twospotted Spider Mite

In this test, Pinto bean seedlings are infested with female twospotted spider mites; about 3-4 hours are allowed for egg deposition. Plants are then dipped in TEPP (tetraethylpyrophosphate-commercial emulsifiable concentrate (EC)) solution containing 936 ppm of active ingredient. TEPP kills motile forms on the leaf and promptly degrades without effecting the egg stage. Two to three hours after TEPP treatment the plants are again dipped — this time into a candidate insecticide solution. The test plants are maintained for 7 to 10 days. Termination of exposure is determined by the time required to attain complete hatch in the untreated check. Ovicidal activity test results are given in Table IV.

e. Insecticidal Activity Against House Flies and German Cockroaches

Compounds of this invention were tested in a Level I test at 5 mg. of active compounds/milliliter of a solution of 40% acetone — 60% water.

In this test a group of ten house flies (*Musca domestica* Linnaeus) were completely immersed in 25 ml. of the insecticidal test solution. After 10 seconds of immersion, the test solution is removed. The house flies are then transferred to holding cages lines with paper toweling. In the case of the house flies, the knockdown counts were recorded 10 minutes after termination of the immersion. The percent kill was recorded after 18-24 hours.

The same Level I test technique was employed using male German cockroaches [*Blattella germanica* (Linnaeus)]. In this case, the knockdown counts were recorded 30 minutes after the termination of the immersion.

In a Level II test the compounds of this invention were tested for insecticidal activity against female house flies (resistant) and male German cockroaches. Ten insects were anesthetized with carbon dioxide and placed in a container for about 2 hours, during which time the insects recovered to normal activity. The container confining the insects is fitted with a plunger which is used to force the insects against a nylon mesh at one end of the container. One microliter of an acetone solution containing one microgram of the candidate insecticide was applied topically to each insect. The plunger was withdrawn and the insects were allowed to move freely about the container. Knockdown counts were recorded 10 minutes after treatment of house flies and 30 minutes after treatment of cockroaches. Test results involving house flies and German cockroaches are set forth in Table V.

Table I

| | Initial Insecticidal Activity | | | |
| | | % Kill | | |
| Compound of Example | Conc/ ppm | Milkweed Bug | Plum Curculio | Confused Flour Beetle | Granary Weevil |
| --- | --- | --- | --- | --- | --- |
| 1(c) | 1250 | 100 | 100 | 33 | 100 |
| | 156 | 100 | 15 | 15 | 100 |
| | 39 | 100 | 0 | 14 | 30 |
| control | | 10 | 0 | 10 | 0 |
| 2(d) | 1250 | 100 | 100 | 72 | 100 |
| | 156 | 100 | 20 | 2 | 100 |
| | 39 | 100 | 0 | 0 | 88 |
| control | | 5 | 0 | 0 | 63* |
| 3(c) | 1250 | 100 | 77 | 55 | 100 |
| | 156 | 100 | 5 | 2 | 90 |
| | 39 | 85 | 5 | 0 | 70 |
| control | | 5 | 0 | 0 | 63* |
| 4(c) | 1250 | 100 | 10 | 65 | — |
| | 156 | 100 | 50 | 8 | — |
| | 39 | 90 | 0 | 0 | — |
| control | | 0 | 0 | 0 | — |
| 5(c) | 1250 | 100 | 100 | 78 | — |
| | 156 | 100 | 85 | 0 | — |
| | 39 | 100 | 50 | 0 | — |
| 6(c) | 1250 | 100 | 100 | 18 | — |
| | 156 | 100 | 45 | 0 | — |
| | 39 | 95 | 0 | 0 | — |
| 7(c) | 1250 | 95 | 65 | 0 | — |
| | 156 | 70 | 50 | 0 | — |
| | 39 | 5 | 20 | 0 | — |
| 8(c) | 1250 | 100 | 100 | 50 | — |
| | 156 | 100 | 45 | 0 | — |
| | 39 | 100 | 0 | 0 | — |
| control** | — | 5 | 0 | 0 | — |
| 9(c) | 1250 | 100 | 94 | 8 | — |
| | 156 | 100 | 5 | 3 | — |
| | 39 | 6 | 0 | 0 | — |
| control | — | 0 | 0 | 0 | — |

| | Initial Insecticidal Activity | | | |
| | | % Kill | | |
| Compound of Example | Conc/ ppm | Mexican Bean Beetle | Pea Aphid | Southern Armyworm | Twospotted Spider Mite |
| --- | --- | --- | --- | --- | --- |
| 1(c) | 1250 | 100 | 100 | 95 | 100 |
| | 156 | 100 | 100 | 20 | 37 |
| | 39 | 100 | 0 | 6 | 21 |
| control | | 0 | 0 | 0 | 5 |
| 2(d) | 1250 | 100 | 100 | 100 | 100 |
| | 156 | 100 | 100 | 54 | 91 |
| | 39 | 100 | 86 | 0 | 39 |
| control | | 0 | 0 | 0 | 3 |
| 3(c) | 1250 | 100 | 100 | 100 | 100 |
| | 156 | 100 | 100 | 22 | 86 |
| | 39 | 100 | 31 | 0 | 32 |
| control | | 0 | 0 | 0 | 3 |
| 4(c) | 1250 | 95 | 100 | 100 | 100 |
| | 156 | 100 | 100 | 29 | 37 |
| | 39 | 86 | 33 | 0 | 8 |
| control | — | 0 | 0 | 0 | 0 |

Table I-continued

| Compound | Conc | | | | |
|---|---|---|---|---|---|
| 5(c) | 1250 | 100 | 100 | 100 | 100 |
| | 156 | 100 | 100 | 69 | 47 |
| | 39 | 78 | 0 | 0 | 6 |
| 6(c) | 1250 | 100 | 100 | 100 | 100 |
| | 156 | 94 | 60 | 73 | 23 |
| | 39 | 100 | 28 | 6 | 6 |
| 7(c) | 1250 | 100 | 0 | 31 | 5 |
| | 156 | 94 | 0 | 29 | 6 |
| | 39 | 95 | 11 | 0 | 1 |
| 8(c) | 1250 | 100 | 100 | 100 | 100 |
| | 156 | 100 | 83 | 59 | 36 |
| | 39 | 100 | 0 | 0 | 5 |
| control** | — | 0 | 0 | 0 | 3 |
| 9(c) | 1250 | 100 | 100 | 79 | 98 |
| | 156 | 100 | 0 | 8 | 6 |
| | 39 | 60 | 0 | 0 | 3 |
| control | — | 0 | 0 | 0 | — |

*The control was contaminated; test invalid.
**Compounds of Examples 5(c)–8(c) examined in same test, with one control.

Table II

Seven-Day Residual Insecticidal Activity
% Kill

| Compound of Example | Conc/ ppm | Milkweed Bug | Plum Curculio | Confused Flour Beetle | Granary Weevil |
|---|---|---|---|---|---|
| 1(c) | 1250 | 100 | 85 | 23 | 100 |
| | 156 | 100 | 22 | 18 | 97 |
| | 39 | 55 | 0 | 10 | 8 |
| control | | 5 | 0 | 0 | 15 |
| 2(d) | 1250 | 100 | 86 | 38 | — |
| | 156 | 100 | 5 | 2 | — |
| | 39 | 56 | 0 | 0 | — |
| control | | 10 | 0 | 0 | — |
| 3(c) | 1250 | 100 | 95 | 78 | — |
| | 156 | 90 | 10 | 0 | — |
| | 39 | 5 | 5 | 0 | — |
| control | | 10 | 0 | 0 | — |
| 4(c) | 1250 | 100 | 19 | 0 | — |
| | 156 | 95 | 0 | 0 | — |
| | 39 | 75 | 0 | 0 | — |
| control | — | 10 | 0 | 0 | — |
| 5(c) | 1250 | 100 | 80 | 0 | — |
| | 156 | 100 | 0 | 0 | — |
| | 39 | 0 | 0 | 0 | — |
| 6(c) | 1250 | 100 | 100 | 0 | — |
| | 156 | 25 | 0 | 0 | — |
| | 39 | 5 | 0 | 0 | — |
| 7(c) | 1250 | 60 | 0 | 0 | — |
| | 156 | 21 | 0 | 0 | — |
| | 39 | 26 | 5 | 0 | — |
| 8(c) | 1250 | 100 | 100 | 12 | — |
| | 156 | 100 | 5 | 0 | — |
| | 39 | 95 | 0 | 0 | — |
| control* | — | 0 | 0 | 0 | — |
| 9(c) | 1250 | 100 | 0 | 12 | — |
| | 156 | 85 | 0 | 0 | — |
| | 39 | 0 | 0 | 0 | — |
| control | — | 0 | 0 | 0 | — |

Seven-Day Residual Insecticidal Activity
% Kill

| Compound of Example | Conc/ ppm | Mexican Bean Beetle | Pea Aphid | Southern Armyworm | Twospotted Spider Mite |
|---|---|---|---|---|---|
| 1(c) | 1250 | 86 | 100 | 95 | 9 |
| | 156 | 89 | 0 | 5 | 1 |
| | 39 | 38 | 0 | 0 | 2 |
| control | | 0 | 0 | 0 | 3 |
| 1(d) | 1250 | 100 | 56 | 60 | 1 |
| | 156 | 76 | 0 | 0 | 0 |
| | 39 | 50 | 0 | 0 | 0 |
| control | | 0 | 0 | 0 | 3 |
| 3(c) | 1250 | 100 | 73 | 0 | 5 |
| | 156 | 92 | 0 | 0 | 0 |
| | 39 | 28 | 0 | 0 | <1 |
| control | | 0 | 0 | 0 | 3 |
| 4(c) | 1250 | 100 | 100 | 60 | 2 |
| | 156 | 62 | 0 | 5 | 0 |
| | 39 | 27 | 0 | 0 | 0 |
| control | | 0 | 0 | 0 | 0 |
| 5(c) | 1250 | 100 | 62 | 61 | 2 |
| | 156 | 70 | 0 | 0 | 0 |
| | 39 | 6 | 0 | 0 | 2 |
| 6(c) | 1250 | 100 | 5 | 7 | 0 |
| | 156 | 38 | 0 | 0 | 1 |
| | 39 | 6 | 0 | 0 | 0 |
| 7(c) | 1250 | 100 | 0 | 0 | 0 |
| | 156 | 89 | 0 | 0 | 0 |
| | 39 | 20 | 0 | 0 | 1 |
| 8(c) | 1250 | 100 | 0 | 43 | 0 |
| | 156 | 93 | 0 | 0 | 0 |
| | 39 | 12 | 0 | 0 | 0 |
| control* | — | 0 | 5 | 0 | 0 |
| 9(c) | 1250 | 100 | 0 | 25 | 0 |
| | 156 | 100 | 0 | 0 | 0 |
| | 39 | 8 | 6 | — | — |
| control | — | 0 | 0 | 0 | — |

*Compounds of Examples 5(c)–8(c) examined in same test, with one control.

Table III

Systemic Insecticidal Activity (Soil/Water)
% Kill

| Compound of Example | Conc ppm | Mexican Bean Beetle | Pea Aphid | Southern Armyworm | Twospotted Spider Mite |
|---|---|---|---|---|---|
| 1(c) | 156 | 95 | 100 | 92 | 8 |
| | 39 | 100 | 100 | 0 | 2 |
| control | | 0 | 0 | 0 | 5 |
| 2(d) | 156 | 100 | 80 | 100 | 18 |
| | 39 | 85 | 11 | 94 | 2 |
| | 10 | 20 | 0 | 0 | 0 |
| 3(c) | 156 | 94 | 79 | 95 | 5 |
| | 39 | 44 | 0 | 0 | <1 |
| | 10 | 44 | 0 | 0 | <1 |
| control* | | 0 | 0 | 0 | 1 |
| 4(c) | 156 | 94 | 100 | 42 | 7 |
| | 39 | 65 | 93 | 0 | 0 |
| | 10 | 7 | 0 | 0 | 0 |
| control | — | 0 | 0 | 0 | 0 |
| 5(c) | 156 | 100 | 100 | 100 | 24 |
| | 39 | 100 | 0 | 60 | 7 |
| 6(c) | 156 | 100 | 100 | 100 | 19 |
| | 39 | 100 | 100 | 28 | 4 |
| 7(c) | 156 | 100 | 0 | 0 | 1 |
| | 39 | 45 | 0 | 0 | 4 |
| 8(c) | 156 | 100 | 100 | 57 | 13 |
| | 39 | 67 | 0 | 20 | 4 |
| control** | — | 0 | 0 | 0 | 1 |
| 9(c) | 312 | — | — | 80 | 2 |
| | 156 | 65 | 100 | 21 | 0 |
| | 39 | 0 | 0 | 0 | 0 |
| | 10 | 0 | 0 | — | — |
| | 5 | 0 | 0 | — | — |
| control | — | 0 | 5 | 0 | 0 |

*Compounds of Examples 2(d) and 3(c) examined in same test, with one control.
**Compounds of Examples 5(c)–8(c) examined in same test, with one control.

Table IV

Ovicidal Activity Against the Twospotted Spider Mite

| Compound of Example | Conc/ ppm | % Kill |
|---|---|---|
| 1(c) | 1250 | 72 |
| | 156 | 0 |
| | 39 | 0 |
| control | — | 1 |
| 2(d) | 1250 | 80 |
| | 156 | 2 |
| control | — | 0 |
| 3(c) | 1250 | 70 |
| | 156 | 0 |
| control | — | 0 |
| 4(c) | 1250 | 66 |
| | 156 | 0 |
| control | — | 0 |
| 5(c) | 1250 | 38 |
| | 156 | 0 |
| 6(c) | 1250 | 91 |
| | 156 | 0 |
| 7(c) | 1250 | 0 |
| | 156 | 0 |
| 8(c) | 1250 | 26 |
| | 156 | 0 |
| control* | — | 0 |
| 9(c) | 1250 | 94 |
| | 156 | 0 |
| control | — | 0 |

*Compounds of Examples 5(c)–8(c) were examined in same test, with one control.

Table V

Insecticidal Activity Against House Flies and German Cockroaches

| Compound of Example | | Level I Tests % Knockdown | % Kill | Level II Tests % Knockdown | % Kill |
|---|---|---|---|---|---|
| 1(c) | HF | 100 | 100 | 0 | 20 |
|      | GC | 100 | 100 | 0 | 0 |
| 2(d) | HF | 100 | 100 | 0 | 40 |
|      | GC | 100 | 100 | 0 | 10 |
| 3(c) | HF | 100 | 100 | 0 | 40 |
|      | GC | 100 | 100 | 0 | 0 |
| 4(c) | HF | — | — | — | — |
|      | GC | — | — | — | — |
| 5(c) | HF | 100 | 100 | 0 | 38 |
|      | GC | 100 | 100 | 0 | 0 |
| 6(c) | HF | 100 | 100 | 0 | 27 |
|      | GC | 100 | 100 | 0 | 0 |
| 7(c) | HF | 40 | 0 | — | — |
|      | GC | 0 | 0 | — | — |
| 8(c) | HF | 100 | 100 | 0 | 33 |
|      | GC | 100 | 100 | 0 | 0 |

HF — House Flies
GC — German Cockroaches

The compounds of this invention are characterized by advantageous mammalian toxicity values when compared with values for related compounds. This is shown by comparative values obtained with Wistar derived albino rats in 14-day tests. The animals were fed, housed and watered in accordance with standard laboratory procedures. The 14-day $LD_{50}$ determination was estimated in accord with the method of Miller and Tainter (Experimental Biology and Medicine, 57, pp. 261–264, 1944). Typical comparative mammalian toxicity values are given in Table VI below.

Table VI

| Compound of | $LD_{50}$ |
|---|---|
| Example 1 (c) | 146.00 (±) 13.25 mg/kg |
| 2 (d) | 152.00 (±) 20.50 mg/kg |
| carbofuran | 12.20 (±) 2.02 mg/kg |

The compounds of this invention are insoluble in water and can be formulated with the usual additives and extenders used in the preparation of insecticidal compositions. The toxicants of this invention, like most insecticidal agents, are generally not applied full strength, but are incorporated with the adjuvants and carriers normally employed for facilitating the dispersion of active ingredients, recognizing the accepted fact that the formulation and mode of application of a toxicant can affect the activity of the material. The present compounds can be applied, for example, as a spray, dust, or granule, to the area in which pest control is desired, the choice of application varying of course with the type of insect and the environment. Thus, the compounds can be formulated as granules of large particle size, as powdery dusts, as wettable powders, as emulsifiable concentrates, as solutions, and the like.

Dusts are admixtures of the active ingredients with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as dispersants and carriers for the toxicant. These finely divided solids have an average particle size of less than about 50 microns. A typical dust formulation useful herein contains 10.0 parts of the compound of EXAMPLE 1(c), 30.0 parts of bentonite clay, and 60.0 parts of talc.

The compounds of the present invention can be made into liquid concentrates by solution, dispersion or emulsion in suitable liquids, and into solid concentrates by admixtures with talc, clays and other known solid carriers used in the insecticide art. The concentrates are compositions containing about 5–50% toxicant, and 95–50% inert material which includes dispersing agents, emulsifying agents, and wetting agents. The concentrates are diluted for practical application, with water or other liquid for sprays or with additional solid carrier for use as dusts. Typical carriers for solid concentrates (also called wettable powders) include fuller's earth, kaolin clays, silicas, and other highly absorbent, readily wet inorganic diluents. A solid concentrate formulation useful herein contains 1.5 parts each of sodium lignosulfonate and sodium laurylsulfate as wetting agents, 25.0 parts of the compound of EXAMPLE 3(c) and 72.0 parts of bentonite clay.

Useful liquid concentrates include the emulsifiable concentrates, which are homogeneous liquid or paste compositions readily dispersed in water or other dispersant, and can consist entirely of the toxicant with a liquid or solid emulsifying agent, or can also contain a liquid carrier such as xylene, heavy aromatic naphthas, isophorone and other non-volatile organic solvents. For application, these concentrates are dispersed in water or other liquid carrier, and normally applied as a spray to the area to be treated.

Typical wetting, dispersing or emulsifying agents used in insecticidal formulations include, for example, the alkyl and alkylaryl sulfonates and sulfates and their sodium salts; alkylamide sulfonates, including fatty methyl taurides; alkylaryl polyether alcohols; sulfated higher alcohols; polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1–15% by weight of the insecticidal composition.

Other useful formulations include simple solutions of the active ingredient in a solvent in which it is completely soluble at the desired concentration, such as acetone or other organic solvents.

The compounds of this invention can also be applied as aerosols. In such case, a compound can be dissolved in any suitable solvent and the resulting solution can be dispersed in dichlorofluoromethane or other chlorofluoroalkane having a boiling point below room temperature at ambient pressures.

The concentration of the toxicant in the dilution generally used for application is normally in the range of from about 2% to about 0.001%. Many variations of spraying and dusting compositions in the art can be used, by substituting a compound of this invention into compositions known or apparent to the art.

A wide range of active ingredient concentration can be employed in insecticidal compositions intended for full-strength and diluted compositions. A diluted formulation ready for spraying can contain between about 0.001 to about 0.01 percent of active ingredient. Full-strength aerosols or granular formulations can contain as little as about 0.5 percent, while paste formulations can contain as much as 95 percent active ingredient. Thus, a range of from about 0.001 to about 95 percent is employed.

Insecticidal compositions can be formulated and applied with other active ingredients, including other insecticides, nematicides, acaricides, fungicides, plant regulators, fertilizers, etc. In applying the chemicals, it is obvious that an effective amount and concentration of a [(N-disubstituted phosphoro) (N-alkyl)aminosulfenyl]-substituted carbamic acid ester of 2,3-dihydro-7-benzofuranol should be employed.

It is apparent that many modifications can be made in the structure, preparation, formulation and application of the compounds of this invention, without departing from the spirit and scope of the invention and of the following claims.

I claim:

1. A compound of the formula

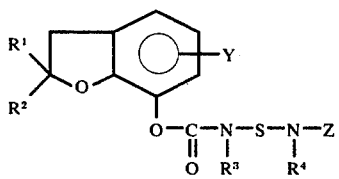

wherein
$R^1$ and $R^2$ are each hydrogen or lower alkyl ($C_1$ to $C_6$) and can be the same or different;
$R^3$ is lower alkyl ($C_1$ to $C_6$ [alkyl]);
$R^4$ is hydrogen, lower alkyl ($C_1$ to $C_6$), [cycloalkyl ($C_3$-$C_8$), aralkyl or aryl] phenyl-lower alkyl ($C_1$ to $C_6$) or phenyl; and

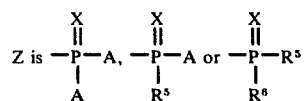

where
X is O or S, A is $OR^5$, [$SR^5$, $NHR^5$ or $NR^5R^6$], and $R^5$ and $R^6$ are each lower alkyl ($C_1$ to $C_6$) [, cycloalkyl] or [aryl] phenyl and can be the same or different; and
Y is hydrogen, halo or methyl.

2. A compound of the formula of claim 1, wherein $R^1$ is methyl.

3. A compound of the formula of claim 1, wherein $R^1$ and $R^2$ are each methyl.

4. A compound of the formula of claim 1, wherein $R^1$, $R^2$, $R^3$ and $R^4$ are methyl.

5. A compound of the formula of claim 1, wherein

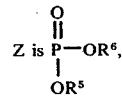

and $R^5$ and $R^6$ are each lower alkyl ($C_1$ to $C_6$) or phenyl and can be the same or different.

6. A compound of the formula of claim 1, wherein

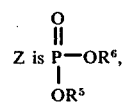

$R^5$ and $R^6$ being alkyl.

7. 2,3-Dihydro-2,2-dimethyl-7-benzofuranyl[(N-diethoxyphosphinyl) (N-methyl)aminosulfenyl][methyl]carbamate of the formula of claim 1.

8. 2,3-Dihydro-2,2-dimethyl-7-benzofuranyl[(N-di-n-propoxyphosphinyl) (N-methyl)aminosulfenyl][methyl]carbamate of the formula of claim 1.

9. 2,3-Dihydro-b 2,2-dimethyl-7-benzofuranyl[(N-di-n-propoxyphosphinyl) (N-n-propyl)aminosulfenyl][methyl]carbamate of the formula of claim 1.

10. 2,3-Dihydro-2,2-dimethyl-7-benzofuranyl[(N-diethoxyphosphinyl) (N-n-propyl)aminosulfenyl][methyl]carbamate of the formula of claim 1.

11. An insecticidal composition comprising an insecticidally effective amount of a compound of claim 1 in admixture with an extender.

12. An insecticidal composition of claim 11, wherein the amount of said compound is from about 0.001 to about 95 percent by weight of the composition.

13. The method of controlling insects which comprises applying to the sites of infestation a composition containing an insecticidally effective amount of a compound of claim 1.

14. The method of claim 13, wherein the amount of said compound is from about 0.001 to about 95 percent by weight of the composition.

* * * * *

UNITED STATES PATENT OFFICE
CERTIFICATE OF CORRECTION

PATENT NO. : 4,024,277

DATED : May 17, 1977

INVENTOR(S) : John Francis Engel

It is certified that error appears in the above-identified patent and that said Letters Patent are hereby corrected as shown below:

Column 13, line 29, "($C_1$ to $C_6$ [alkyl]);" should read --($C_1$ to $C_6$);--; line 30, "[cycloalkyl" should be deleted; line 31, "($C_3$-$C_8$), aralkyl or aryl]" should be deleted; line 40, "[$SR^5$, $NHR^5$ or $NR^5R^6$]," should be deleted; line 41, "[,cycloal-]" should be deleted; line 42, "kyl] or [aryl]phenyl" should read --or phenyl--.

Signed and Sealed this

Fifteenth Day of November 1977

[SEAL]

Attest:

RUTH C. MASON
Attesting Officer

LUTRELLE F. PARKER
Acting Commissioner of Patents and Trademarks